(12) United States Patent
Cull

(10) Patent No.: US 7,025,741 B2
(45) Date of Patent: Apr. 11, 2006

(54) ARTERIOVENOUS ACCESS VALVE SYSTEM AND PROCESS

(75) Inventor: David L. Cull, Greenville, SC (US)

(73) Assignee: Creativasc Medical LLC, Greenville, SC (US)

( * ) Notice: Subject to any disclaimer, the term of this patent is extended or adjusted under 35 U.S.C. 154(b) by 0 days.

(21) Appl. No.: 10/456,697

(22) Filed: Jun. 6, 2003

(65) Prior Publication Data

US 2004/0249334 A1 Dec. 9, 2004

(51) Int. Cl.
*A61M 37/00* (2006.01)
*A61M 5/00* (2006.01)
*A61M 39/00* (2006.01)
*A61F 2/06* (2006.01)
*A61B 17/08* (2006.01)

(52) U.S. Cl. .................. 604/9; 604/4.01; 604/5.01; 604/8; 604/6.16; 604/96.01; 604/288.02; 623/1.13; 623/1.24; 623/1.42; 606/153

(58) Field of Classification Search .............. 604/4.01, 604/5.01–5.04, 6.01, 6.16, 7–10, 28, 29, 604/500, 507, 523, 264, 96.01, 891.1, 103.01–103.02, 604/101.04, 164.01, 164.02, 164.03, 164.04, 604/164.09, 167.01, 167.02, 167.03, 173–175, 604/181–184, 532–539; 606/191, 194, 151, 606/153, 158; 623/3.1, 3.26, 1.1, 1.36, 1.42, 623/1.25, 1.24; 210/645–646, 650
See application file for complete search history.

(56) References Cited

U.S. PATENT DOCUMENTS

| 3,730,186 A | 5/1973 | Edmunds, Jr. et al. |
|---|---|---|
| 3,998,222 A | 12/1976 | Shihata |
| 4,828,544 A | 5/1989 | Lane et al. |
| 5,034,265 A | 7/1991 | Hoffman et al. |
| 5,562,617 A | 10/1996 | Finch, Jr. et al. |
| 5,797,879 A * | 8/1998 | DeCampli ............... 604/93.01 |
| 5,879,320 A | 3/1999 | Cazenave |
| 5,976,178 A | 11/1999 | Goldsteen et al. |
| 6,053,891 A | 4/2000 | DeCampli |
| 6,053,901 A * | 4/2000 | Finch et al. ............... 604/502 |
| 6,056,717 A | 5/2000 | Finch et al. |
| 6,086,553 A | 7/2000 | Akbik |
| 6,102,884 A | 8/2000 | Squitieri |
| 6,352,521 B1 | 3/2002 | Prosl |
| 6,595,941 B1 | 7/2003 | Blatter |
| 6,656,151 B1 | 12/2003 | Blatter |

OTHER PUBLICATIONS

Search Report and Written Opinion for PCT/US04/10209, Nov. 19, 2004.

* cited by examiner

*Primary Examiner*—Patricia Bianco
(74) *Attorney, Agent, or Firm*—Dority & Manning, P.A.

(57) ABSTRACT

An arteriovenous graft system is described. The arteriovenous graft system includes an arteriovenous graft that is well suited for use during hemodialysis. In order to minimize or prevent arterial steal, at least one valve device is positioned at the arterial end of the arteriovenous graft. In one embodiment, for instance, the arteriovenous graft system includes a first valve device positioned at the arterial end and a second valve device positioned at the venous end. In one embodiment, the valve devices may include an inflatable balloon that, when inflated, constricts and closes off the arteriovenous graft. By minimizing or preventing arterial steal, other complications associated with arteriovenous grafts are also avoided. For instance, the present invention is also well suited to preventing arteriovenous graft thrombosis, eliminating dialysis needle hole bleeding, and eliminating or minimizing arteriovenous graft pseudoaneurism formation.

37 Claims, 7 Drawing Sheets

ARTERIOVENOUS ACCESS VALVE SYSTEM AND PROCESS

BACKGROUND OF THE INVENTION

The function of kidneys, which are glandular organs located in the upper abdominal cavity of vertebrates, is to filter blood and remove waste products. Specifically, kidneys separate water and waste products of metabolism from blood and excrete them as urine through the bladder. Chronic renal failure is a disease of the kidney in which the kidney function breaks down and is no longer able to filter blood and remove waste substances. Should certain toxic waste substances not be removed from the blood, the toxic substances may increase to lethal concentrations within the body.

Hemodialysis is a life-sustaining treatment for patients who have renal failure. Hemodialysis is a process whereby the patient's blood is filtered and toxins are removed using an extracorporeal dialysis machine. For hemodialysis to be effective, large volumes of blood must be removed rapidly from the patient's body, passed through the dialysis machine, and returned to the patient. A number of operations have been developed to provide access to the circulation system of a patient such that patients may be connected to the dialysis machine.

For example, the most commonly performed hemodialysis access operation is a subcutaneous placement of an arteriovenous graft, which is made from a biocompatible tube. The biocompatible tube can be made of, for instance, a fluoropolymer such as polytetrafluoroethylene. One end of the tube is connected to an artery while the other end is connected to a vein. The arteriovenous graft is typically placed either in the leg or arm of a patient.

Blood flows from the artery, through the graft and into the vein. To connect the patient to a dialysis machine, two large hypodermic needles are inserted through the skin and into the graft. Blood is removed from the patient through one needle, circulated through the dialysis machine, and returned to the patient through the second needle. Typically, patients undergo hemodialysis approximately four hours a day, three days a week.

Various problems, however, have been experienced with the use of an arteriovenous graft. For example, arterial steal occurs when excessive blood flow through the arteriovenous graft "steals" blood from the distal arterial bed. Arterial steal can prevent the proper supply of blood from reaching the extremity of a patient.

Various other complications can also occur. For instance, the blood flowing through the arteriovenous graft can often reach turbulent flow rates. This stream of fast moving blood then exits the arteriovenous graft and contacts the vein connected to the graft. This collision between the flow of blood and the vein may cause the development of myointimal hyperplasia which leads to the thickening of the vein walls and a narrowing of the vessel. As the vein narrows, flow through the arteriovenous graft decreases and blood within the graft may ultimately clot.

The cessation of blood flow through the graft caused by clot formation is known as graft thrombosis. Numerous techniques and medications have been studied in attempts to block the development of the scar tissue. Graft thrombosis, however, continues to remain a reoccurring complication associated with the use of arteriovenous grafts.

In view of the above drawbacks, a need currently exists in the art for an arteriovenous graft that can prevent and minimize arterial steal and graft thrombosis. A process for using an arteriovenous graft in minimizing arterial steal and graft thrombosis is also needed.

SUMMARY OF THE INVENTION

In general, the present invention is directed to subcutaneous arteriovenous graft systems and to processes for using the arteriovenous graft systems in a manner that eliminates or at least reduces arterial steal and graft thrombosis. In one embodiment, for instance, the system includes an arteriovenous graft having an arterial end and an opposite venous end. The arterial end is configured to be connected to an artery to form an arterial anastomosis, while the venous end is configured to be connected to a vein to form a venous anastomosis.

In accordance with the present invention, the system includes at least one valve device positioned at the arterial end of the arteriovenous graft. In one embodiment, for instance, the valve device comprises an inflatable balloon. The inflatable balloon is positioned so as to restrict blood flow through the arteriovenous graft when inflated. In general, the valve device should be positioned at the arterial end of the arteriovenous graft as close as possible to the intersection of the graft with an artery. For example, the valve device may be positioned so as to restrict blood flow through the arteriovenous graft at a location that is less than about 10 mm from the intersection of the arteriovenous graft and an artery.

The inflatable balloon of the valve device may have an annular shape that surrounds the arteriovenous graft. The inflatable balloon may also be a separate structure or may be integral with the arteriovenous graft. When integral with the arteriovenous graft, the arteriovenous graft may include a multi-layered segment located at the arterial end. The multi-layered segment may comprise an inner layer and an outer layer. The inner layer constricts the graft when a fluid is fed in between the inner layer and the outer layer. When having an annular shape, the balloon may be surrounded by a rigid collar that serves to assist the balloon in constricting the graft.

In order to inflate and deflate the balloon, in one embodiment, the valve device can further include an injection port in fluid communication with the inflatable balloon. The injection port defines a diaphragm configured to receive a hypodermic needle for injecting fluid into or withdrawing fluid from the balloon. Of particular advantage, the injection port may also be subcutaneously implanted.

In an alternative embodiment, the inflatable balloon may be positioned in operative association with a piston. In this embodiment, when the balloon is inflated, the balloon forces the piston either towards or away from the arteriovenous graft for opening or closing the valve device.

In addition to the use of a valve device containing an inflatable balloon, the valve device may also comprise a magnetically activated piston. In this embodiment, when a magnetic field is placed in close proximity to the valve device, the piston is moved for either opening or closing the valve device. For example, in one embodiment, placing a magnetic field in close proximity to the valve device opens the device which normally remains closed.

In one particular embodiment, the magnetically activated piston may be activated when exposed to a changing magnetic field, such as a pulsing magnetic field. In this embodiment, the valve device may include a coil member configured to convert a changing magnetic field into an electric current. The coil member is in communication with a solenoid. The solenoid is configured to move the piston and open or close the valve device when electric current is received from the coil member.

In one embodiment, the arteriovenous graft system further includes a second valve device positioned at the venous end of the arteriovenous graft. The second valve device may be any suitable valve device as described above. The second valve device, for instance, may be identical to the first valve device or, alternatively, may be different.

In general, for most applications, the second valve device is not exposed or subjected to the same fluid pressures that are exerted on the first valve device. In this regard, the first valve device is designed to restrict or stop fluid flow at relatively high pressures. The second valve device, however, may be a low pressure valve device. In one embodiment, for instance, the second valve device may be a check valve positioned at the venous end of the arteriovenous graft. For example, the second valve device may be formed integral with the arteriovenous graft and may be formed from a membrane that allows fluid flow from the arteriovenous graft and into an adjoining vein but prevents fluid flow from the vein into the arteriovenous graft.

The arteriovenous graft of the present invention is used for hemodialysis. During hemodialysis, two hypodermic needles are inserted into the arteriovenous graft. Blood is removed from the graft using one needle, circulated through a dialysis machine, and returned to the arteriovenous graft through the second needle. When hemodialysis is not being conducted, however, the valve devices of the present invention may be activated in order to minimize arterial steal and prevent thrombosis of the graft.

For example, in one embodiment of the present invention, when the arteriovenous graft system only includes a single valve device at the arterial end, after hemodialysis has ended, the valve device is closed thus preventing blood flow through the graft. After the valve device is closed, a blood compatible fluid may be injected into the graft using a hypodermic needle. As used herein, a blood compatible fluid refers to any fluid that is biocompatible with the circulation system. For example, in one embodiment, the blood compatible fluid is a heparinized saline solution. The saline solution is used to flush the graft after the valve device is closed in order to remove blood from the graft.

In another embodiment, after hemodialysis, the valve device is partially closed to a first position thereby constricting the arteriovenous graft and reducing blood flow through the graft. The patient is then monitored over a period of time, such as days or weeks, and the valve device may be selectively opened or closed from the first position until arterial steal is minimized. In this embodiment, the valve device is closed an amount sufficient to reduce blood flow through the graft without slowing the blood flow to a point where blood clots may form.

As described above, in another embodiment of the present invention, the arteriovenous graft system includes a first valve device at the arterial end and a second valve device at the venous end. In this embodiment, after hemodialysis has ended, the first valve device at the arterial end is closed thereby preventing blood flow through the graft. A hypodermic needle then flushes the graft with a blood compatible fluid evacuating all blood from the graft. After the graft has been flushed with the blood compatible fluid, the second valve device is then closed and the hypodermic needle is removed from the graft.

Other features and aspects of the present invention are discussed in greater detail below.

BRIEF DESCRIPTION OF THE DRAWINGS

A full and enabling disclosure of the present invention is set forth in the specification with reference to the following figures.

Figure 1:
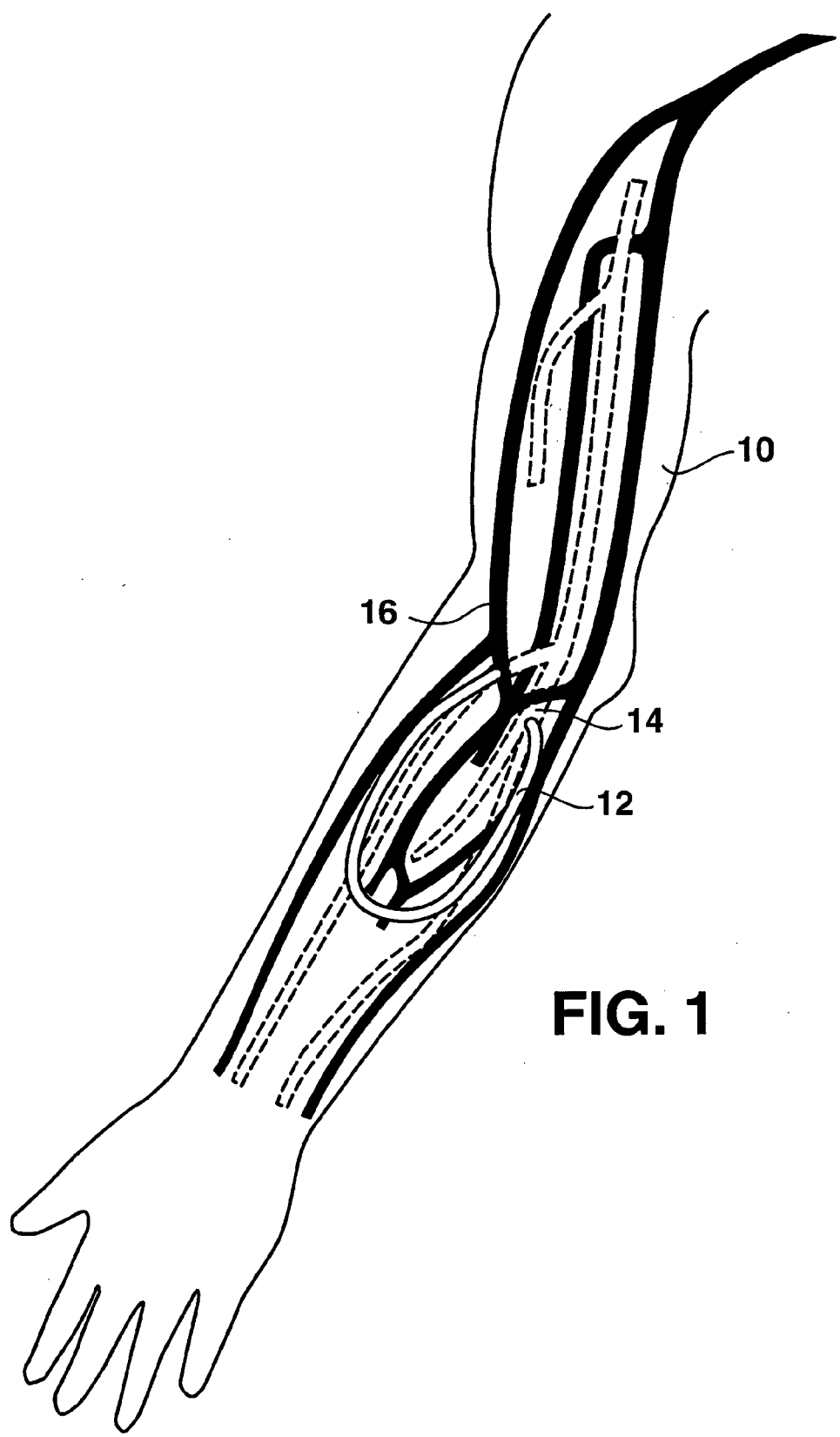
FIG. 1 is a side view with cut away portions of a human arm illustrating the placement of an arteriovenous graft.

Repeated use of reference characters in the present specification and drawings is intended to represent the same or analogous features of the invention.

DETAILED DESCRIPTION OF THE INVENTION

Reference now will be made to the embodiments of the invention, one or more examples of which are set forth below. Each example is provided by way of explanation of the invention, not as a limitation of the invention. In fact, it will be apparent to those skilled in the art that various modifications and variations may be made in the invention without departing from the scope or spirit of the invention. For instance, features illustrated or described as part of one embodiment may be used in another embodiment to yield a still further embodiment. For example, an arteriovenous graft system may include combinations of the valve devices described below. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied in the exemplary construction.

In general, the present invention is directed to an implantable arteriovenous graft system that may be used in carrying out hemodialysis treatments. Although the following description will refer to the arteriovenous graft system being implanted into an arm, it should be understood that the system may be implanted in any suitable location of the body. For example, in other embodiments, the arteriovenous graft system may be implanted into a leg.

In addition to being well suited for carrying out hemodialysis, the arteriovenous graft system of the present invention also prevents or minimizes arterial steal and graft thrombosis. In particular, the arteriovenous graft system is designed to prevent or minimize blood flow through the graft when hemodialysis is not occurring.

Referring to FIG. 1, for purposes of explanation, a right arm 10 of a patient is shown. Selected arteries (shown as dotted pathways) are illustrated in conjunction with selected veins (shown as dark pathways). An arteriovenous graft 12 is shown connected at one end to an artery and at an opposite end to a vein. In particular, the arteriovenous graft 12 is connected to the brachial artery 14 and to the cephalic vein 16.

The arteriovenous graft 12 is made from any suitable biocompatible material. For example, in one embodiment, the graft is made from a fluoropolymer, such as polytetrafluoroethylene, which is commercially available as GOR-TEX™ from the W. L. Gore Company.

Figure 2A:
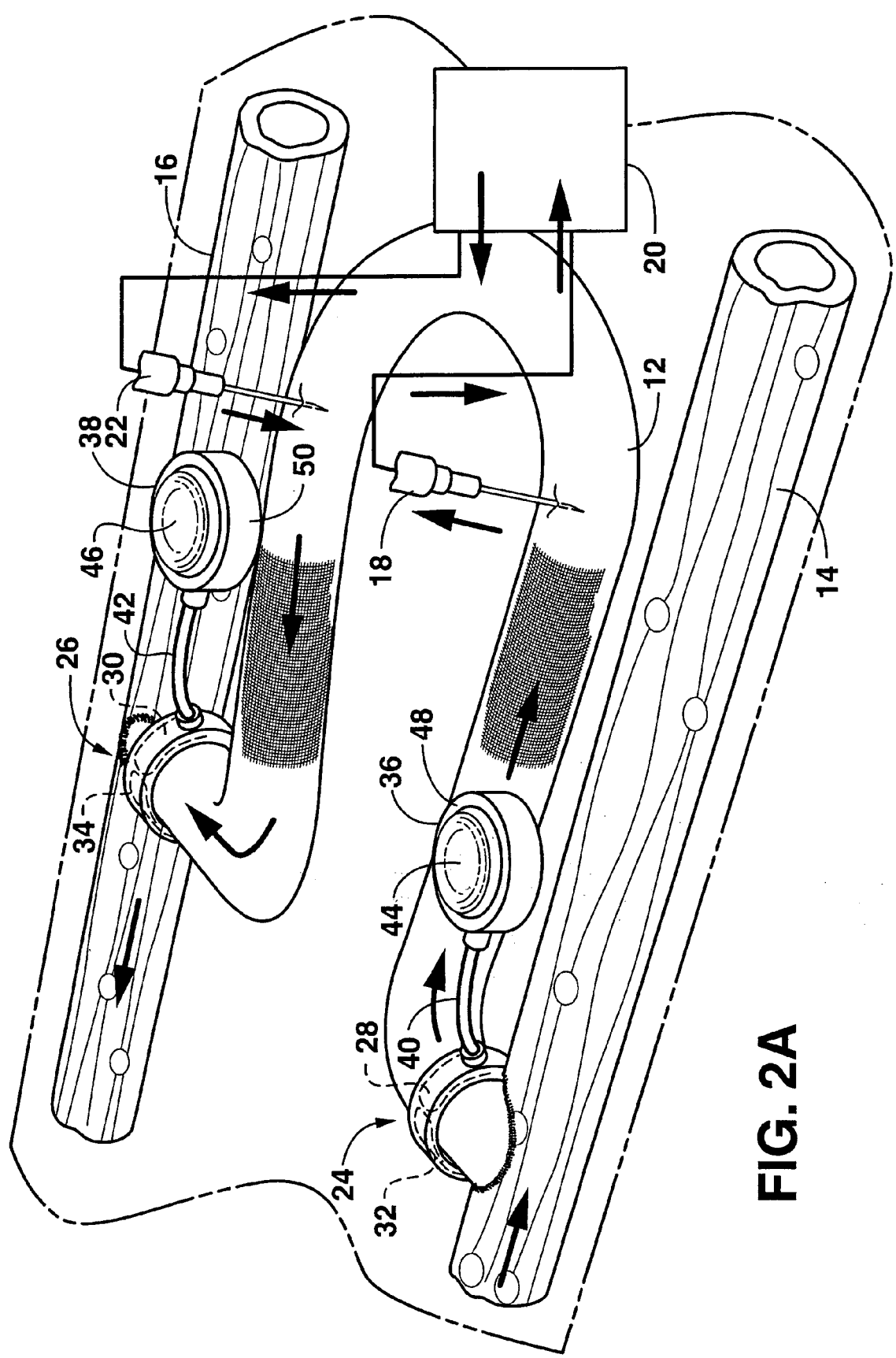
FIGS. 2A, 2B and 2C are perspective views of embodiments of arteriovenous graft systems made in accordance with the present invention.
Figure 2B:
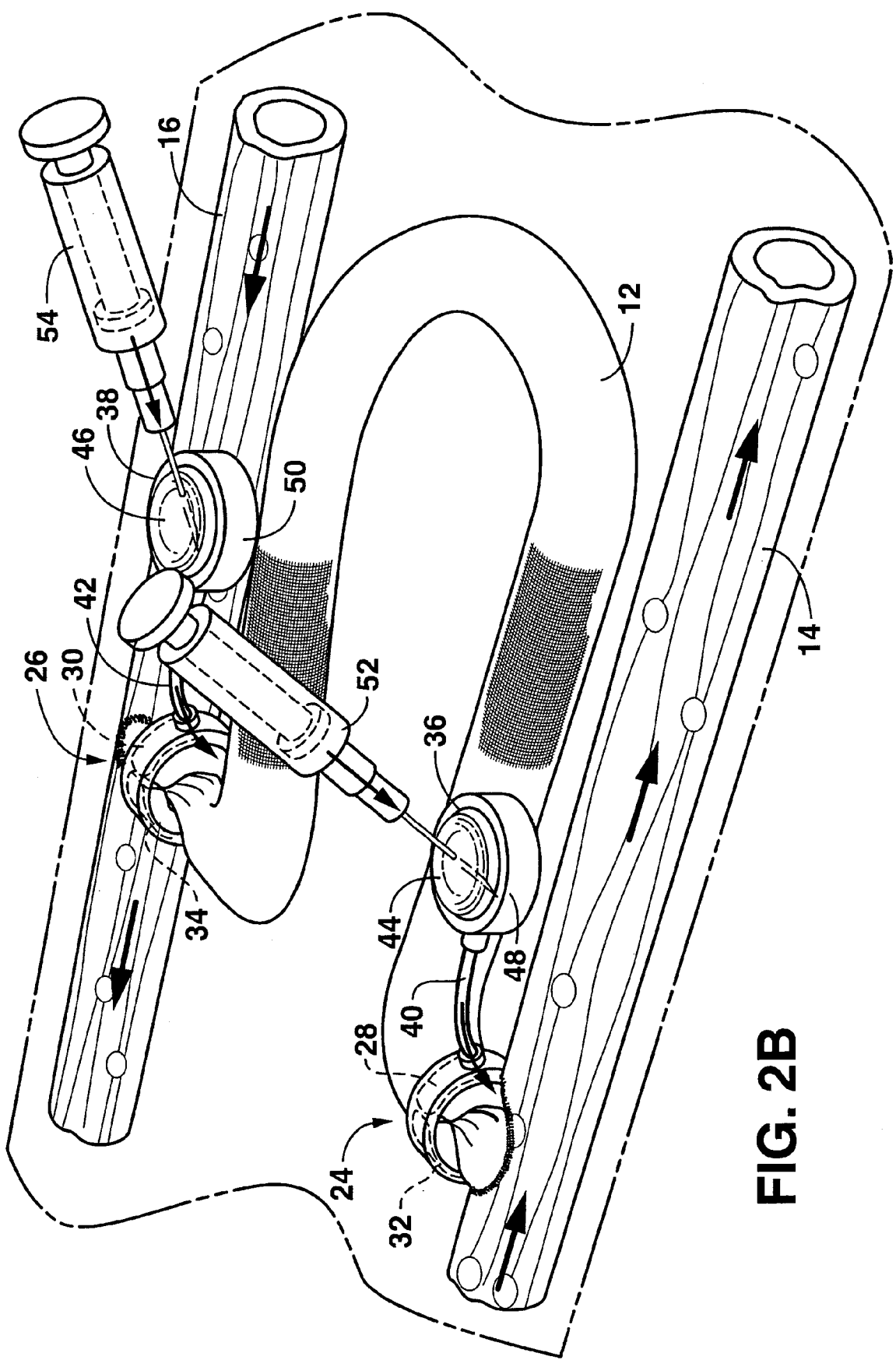

Referring to FIGS. 2A and 2B, one embodiment of an arteriovenous graft system made in accordance with the present invention is shown including an arteriovenous graft 12. As illustrated, the arteriovenous graft 12 is connected to an artery 14 and to a vein 16. In order to carry out hemodialysis, a first hypodermic needle 18 is inserted through the skin and into the arteriovenous graft 12. Blood is removed from the arteriovenous graft 12 through the needle and into a dialysis machine 20. In the dialysis machine, waste materials are removed from the blood. After circulating through the dialysis machine 20, the blood is then fed back into the arteriovenous graft 12 through a second hypodermic needle 22.

In accordance with the present invention, the arteriovenous graft system as shown in FIGS. 2A and 2B further includes at least a first valve device generally 24 positioned at the arterial end of the arteriovenous graft 12. Optionally, the arteriovenous graft system can further include a second valve device generally 26 positioned at the venous end of the arteriovenous graft. The valve devices 24 and 26 are in an open position during normal hemodialysis as shown in FIG. 2A. When hemodialysis has ended, however, the valve devices 24 and 26 are moved to a closed position in order to prevent blood flow through the arteriovenous graft. In this manner, arterial steal is either eliminated or reduced. Further, by reducing arterial steal, graft thrombosis is also prevented.

In addition to minimizing arterial steal and preventing graft thrombosis, the system and the process of the present invention also offer various other advantages. For example, reducing or stopping blood flow through the arteriovenous graft when hemodialysis is not occurring also prevents the graft from bleeding when the hypodermic needles used to carry out hemodialysis are removed from the graft. Hypodermic needles as shown in FIG. 2B, for instance, usually have a relatively large diameter or gauge. Thus, when the needles are removed from a graft, bleeding can occur where the needles have previously been. Needle hole bleeding through the graft can result in the formation of scar tissue and graft pseudoaneurisms. These complications, however, may be prevented through the use of the system of the present invention.

In the embodiment shown in FIG. 2A, the valve devices 26 and 24 each include an inflatable balloon 28 and 30. When inflated, the balloons 28 and 30 constrict the arteriovenous graft 12 for reducing or eliminating blood flow through the graft.

As shown in FIG. 2A, the inflatable balloons 28 and 30, in this embodiment, have an annular shape that surround the arteriovenous graft 12. As shown, each of the inflatable balloons 28 and 30 are also surrounded by a rigid collar 32 and 34. Each collar 32 and 34 may be included in the system in order to maintain each of the balloons 28 and 30 in the proper position. Further, the collars 32 and 34 also serve to bias the balloon towards the arteriovenous graft 12 when inflated. Each collar 32 and 34 may be made from any rigid biocompatible material. For example, the collars 32 and 34 may be made from a metal, such as titanium, or a plastic material.

Figure 2C:
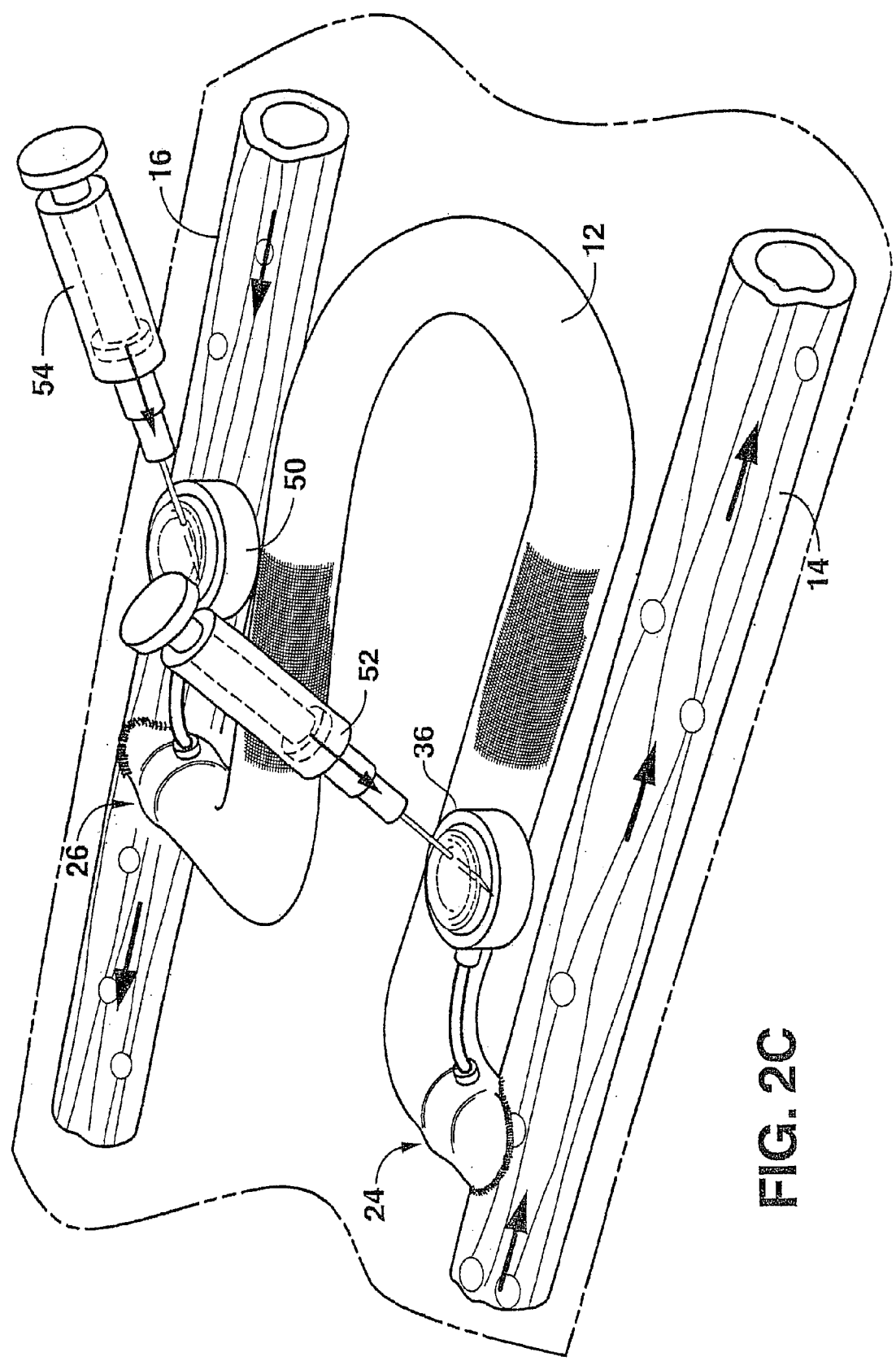

Each annular balloon 28 and 30 may be a separate structure from the arteriovenous graft 12 or may be integral with the graft. When integral with the graft, for instance, the graft may include a multi-layered segment where each of the valve devices is to be located. For example, within the multi-layered segment, the arteriovenous graft 12 may include an outer rigid layer and an inner luminal layer. The balloon 28 and 30 may be formed in between the outer layer and the inner layer. In particular, when a fluid is injected in between the inner and outer layers, the inner layer may expand and constrict the lumen. See FIG. 2C.

In addition to having an annular shape, it should be understood that each balloon 28 and 30 may have any shape sufficient to constrict the arteriovenous graft when inflated. For instance, in another embodiment, each balloon 28 and 30 may be located on one side of the graft 12. When inflated, the balloons 28 and 30 force opposite sides of the graft together.

In order to inflate the balloons 28 and 30, in one embodiment as shown in FIGS. 2A and 2B, each valve device may further include an injection port 36 and 38. For example, as shown in FIG. 2A, injection port 36 may be in fluid communication with the balloon 28 via a tubing 40. Similarly, injection port 38 may be in fluid communication with the balloon 30 via a tubing 42. Each injection port 36 and 38 may be configured to be subcutaneously implanted in a patient.

In the embodiment illustrated in FIG. 2A, injection ports 36 and 38 each include a diaphragm 44 and 46 positioned on one side of a housing 48 and 50. The housings 48 and 50 may be made from any suitable rigid and biocompatible material. For example, each housing may be made from a metal, such as titanium. Each diaphragm 44 and 46, on the other hand, may be made from a material capable of receiving the tip of a hypodermic needle. For example, each diaphragm 44 and 46 may be made from an elastomeric film, such as a silicone membrane.

As shown particularly in FIG. 2B, in order to inflate or deflate the balloons 28 and 30, hypodermic needles 52 and 54 may inject a fluid into each of the injection ports 36 and 38 through the diaphragms 44 and 46. The fluid travels from the injection ports 36 and 38 through the tubing 40 and 42 and into each respective balloon 28 and 30. Similarly, the hypodermic needles 52 and 54 may also be used to withdraw fluid from the balloons 28 and 30.

As shown in FIG. 2B, once inflated, the balloons 28 and 30 constrict the arteriovenous graft 12 at the arterial end and at the venous end. The fluid used to inflate the balloons 28 and 30 may vary depending upon the particular application. The fluid may be, for instance, a gas or liquid. In one embodiment, for instance, a saline solution may be injected into the injection ports 36 and 38 for inflating the balloons. In one embodiment, it may take from about 2 ccs to about 6 ccs of fluid to transition each balloon valve 28 and 30 from an open position to a closed position.

When closed, each valve device should be capable of maintaining its position when exposed to systolic pressure. For example, systolic pressures in arteries may be greater than about 250 mmHg, such as from about 170 mmHg to about 270 mmHg.

In addition to withstanding relatively high fluid pressures, each of the valve devices 24 and 26 should also be constructed so that the valve devices can constrict the arteriovenous graft as close as possible to the intersection of the graft with the artery 14 and the vein 16. For example, the first valve device 24, in one embodiment, constricts the arteriovenous graft at a distance of from about 5 mm from the arterial anastomosis, such as no greater than about 20 mm from the arterial anastomosis. The position of the second valve device 26 in relation to the venous anastomosis may also be within the above defined limits.

The methods for using the arteriovenous graft system of the present invention will now be discussed in relation to a system that contains a single valve device positioned at the arterial end of the graft and a system that contains two valve devices as shown in FIGS. 2A and 2B.

When the arteriovenous graft system of the present invention contains a single valve device positioned at the arterial end, in one embodiment, the valve device may be positioned so as to constrict blood flow through the graft when hemodialysis is not occurring. In this embodiment, arterial steal is not being completely prevented but is being minimized. In particular, the single valve device constricts the graft so that blood flow through the graft continues without clotting but is at a reduced flow rate.

In this embodiment, the patient's condition may need to be monitored over a period of time, such as days or weeks, and the valve device may be adjusted in order to minimize arterial steal without causing a complete blood stoppage. For instance, over several days or weeks, the arteriovenous graft of the patient may be monitored and the valve device may be adjusted so as to gradually increase or decrease the narrowing of the arteriovenous graft. The ultimate position of the valve will vary depending upon the patient and the location of the arteriovenous graft.

In an alternative embodiment, the single valve device may be used to completely close off the arteriovenous graft 12 at the arterial end. In this embodiment, during hemodialysis, the valve device 24 is in the open position and the arteriovenous graft 12 is cannulated with the two dialysis needles 18 and 22 as shown in FIG. 2A. Upon completion of dialysis, a fluid is injected into the injection port 36 of the first valve device causing the balloon 28 to inflate thereby closing the valve device and eliminating arterial blood flow through the graft.

After the valve device is closed, a blood compatible fluid is then injected into the arteriovenous graft 12 through, for instance, a dialysis needle to flush any residual blood out of the graft. The blood compatible fluid can be, for instance, heparinized saline. The residual blood is flushed out of the graft in order to prevent any clotting.

In this embodiment, some residual saline remains in the graft until hemodialysis is once again conducted on the patient. This embodiment should only be used when it is determined that substantially no blood from the vein 16 will flow into the graft once valve device 24 is closed.

In order to prevent any blood flowing from the vein 16 back into the arteriovenous graft 12 after the first valve device 24 has been closed, in one embodiment of the present invention as shown particularly in FIGS. 2A and 2B, the arteriovenous graft system can include the second valve device 26. In this embodiment, the process as described above is repeated. After the arteriovenous graft 12 is flushed with a blood compatible fluid, however, a fluid is injected into the injection port 38 of the second valve device 26 which causes the second valve device to close.

In addition to the valve devices as illustrated in FIGS. 2A and 2B, in other embodiments, other valve devices may also be utilized in the system of the present invention. For example, referring to FIG. 4, another embodiment of a valve device generally 60 is shown in communication with an arteriovenous graft 12. In this embodiment, the valve device 60 includes a fluid chamber 62 in communication with an injection port 64 similar to the injection ports described above. As shown, injection port 64 includes a diaphragm 68 configured to receive fluid from a hypodermic needle 70.

The valve device 60 further includes a piston 72 contained within a housing 74. The piston 72 is positioned below the fluid chamber 62.

In this embodiment, when a fluid is injected from the needle 70 into the injection port 64, the fluid is forced into the fluid chamber 62 via a tube 66. The pressure of the fluid then forces the piston 72 to lower closing the valve and constricting flow through the arteriovenous graft 12.

Figure 4:
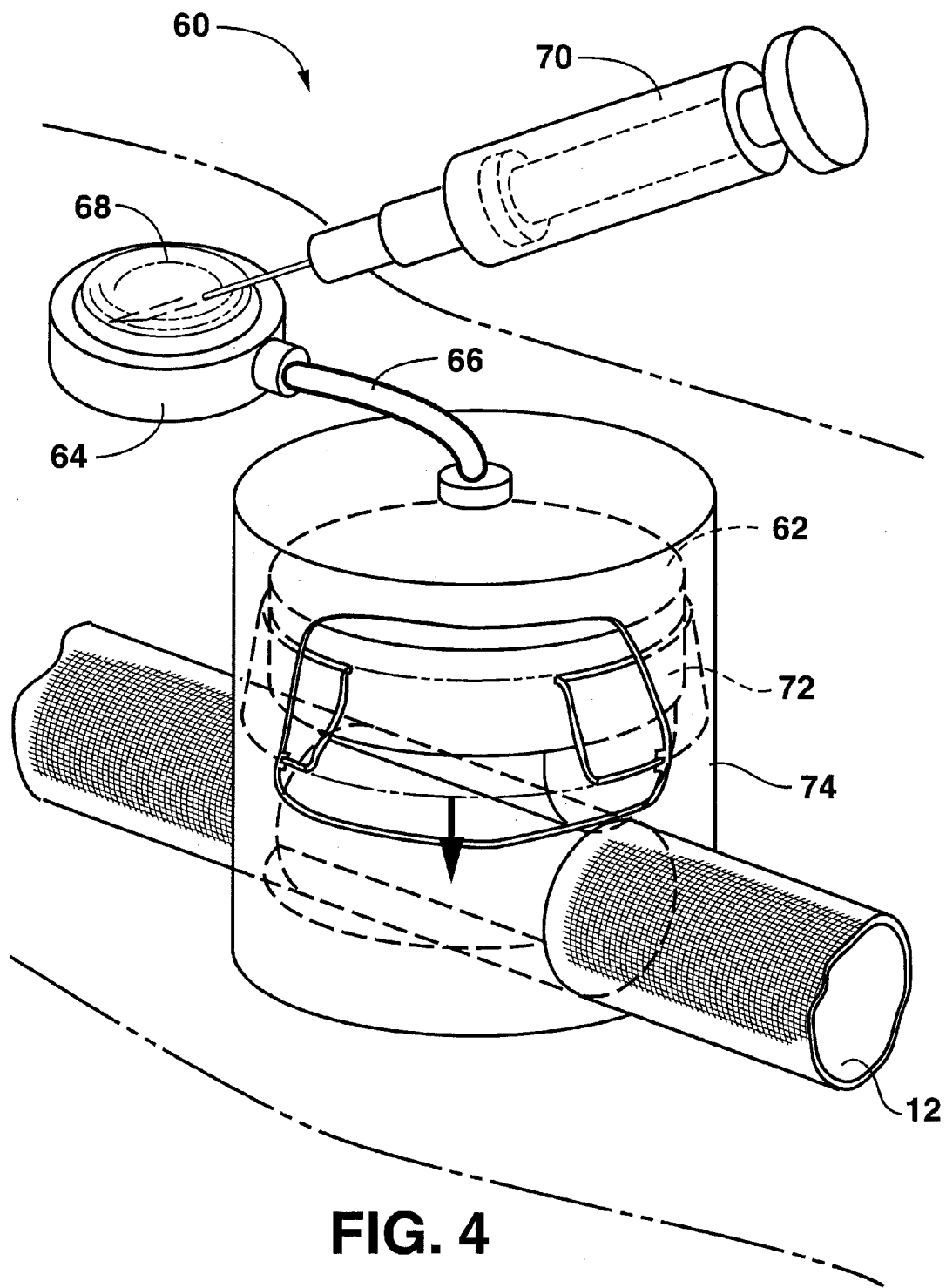
FIG. 4 is a perspective view of another embodiment of a valve device that may be used in the arteriovenous graft system of the present invention.

Valve device 60 as shown in FIG. 4 may be used in a single valve system of the present invention or in a double valve system of the present invention as illustrated in FIG. 2A.

Figure 3:
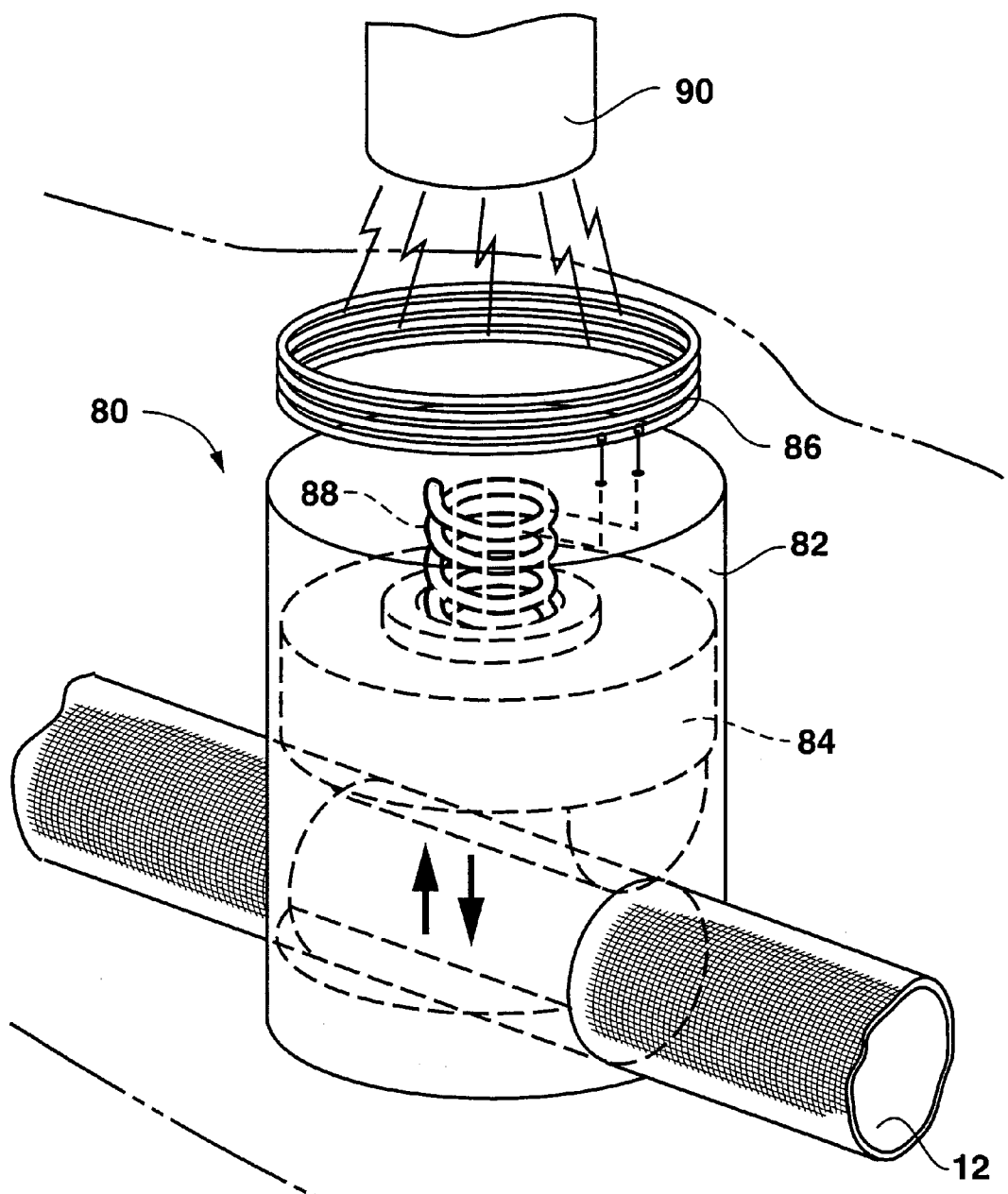
FIG. 3 is a perspective view of one embodiment of a valve device that may be used in the arteriovenous graft system of the present invention.

Referring to FIG. 3, another embodiment of a valve device generally 80 that may be used in the arteriovenous graft system of the present invention is illustrated. In this embodiment, the valve device 80 includes a housing 82 containing a magnetically actuated piston 84. Specifically, the valve device is configured such that the piston 84 moves between an open and closed position when the valve device is contacted with a magnetic field.

In this particular embodiment, the valve device 80 includes a coil member 86. The coil member 86 is configured to convert a pulsating magnetic field into an electric current. As shown, the coil member 86 then supplies the electric current to a solenoid 88. Solenoid 88 then moves the piston 84 to either open or close the valve device.

In order to activate the valve device 80, a magnetic key 90 is placed close to the skin of a patient. In this embodiment, the magnetic key 90 may be an electromagnet that creates a pulsating magnetic field. As described above, the pulsating magnetic field is then converted into an electric current by the coil member 86. The magnetic key 90 may be configured either to open or to close the valve device. In one embodiment, for instance, the valve device 80 may normally be found in a closed position blocking off the arteriovenous graft 12. When the magnetic key 90, however, is placed adjacent to the patient's skin, the valve device 80 then opens allowing blood to circulate through the graft. In other embodiments, however, it should be understood that the valve device may be configured to close when placed adjacent to the magnetic key 90.

In addition to the valve device 80 as shown in FIG. 3, other magnetically activated valves may be used in the system of the present invention. For example, in another embodiment of the present invention, the valve device may include a piston in operative association with a permanent magnet. A ferrous plate may be positioned on the opposite side of the arteriovenous graft. Thus, the permanent magnet contained in the piston is attracted to the ferrous surface for closing off the arteriovenous graft. When a magnet with opposite polarity, however, is placed adjacent to the valve device, the permanent magnet contained within the piston is attracted to the reverse magnetic field causing the valve to open.

Figure 5:
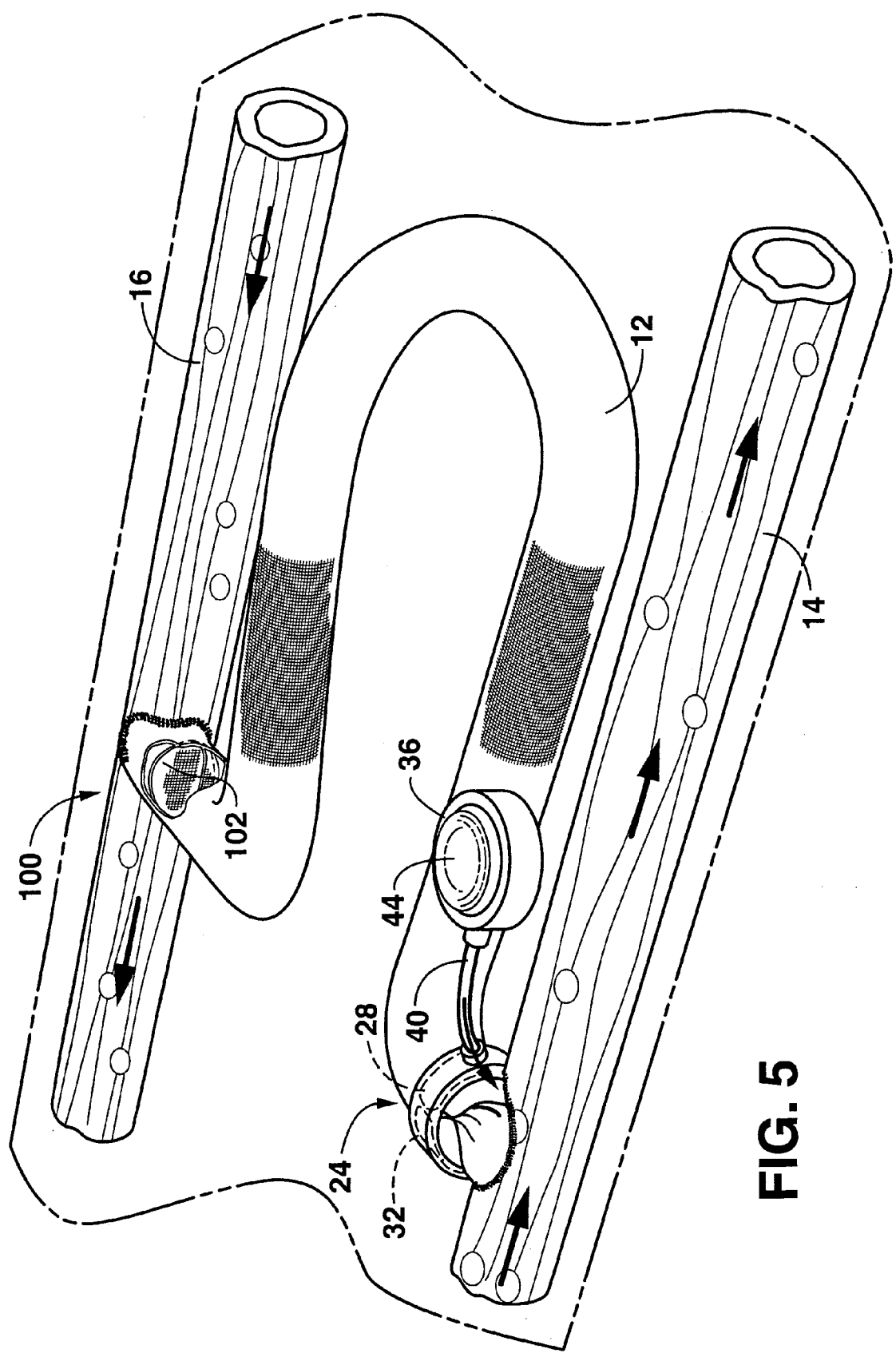
FIG. 5 is a perspective view of still another embodiment of an arteriovenous graft system made in accordance with the present invention.

Referring to FIG. 5, another embodiment of an arteriovenous graft system made in accordance with the present invention is shown. Like reference numerals have been used in order to identify similar features and elements of other embodiments. As shown, in this embodiment, the arteriovenous graft system includes a first valve device generally 24 at the arterial end of the graft similar to the valve device shown in FIGS. 2A and 2B. In particular, the first valve device 24 includes a balloon 28 that is inflated or deflated using an injection port 36. The balloon 28 is for constricting the arteriovenous graft when desired. As explained above, the first valve device 24, for most applications, is capable of maintaining a closed or constricted position on the graft even when exposed to relatively high fluid pressures. In some embodiments, however, these same pressures are not experienced at the venous end of the graft.

In this regard, in this embodiment, the arteriovenous graft 12 includes a second valve device generally 100 that may be described as a low pressure valve device when compared to the first valve device 24.

For example, in one embodiment, the second valve device 100 may be a check valve that allows fluid flow from the graft 12 into the vein 16 but does not permit flow from the vein 16 into the graft 12. In general, any suitable check valve may be used in, accordance with the present invention.

In the embodiment shown in FIG. 5, the second valve device 100 includes a membrane 102 made from, for instance, a polymeric film that is formed or is connected so as to be integral with the arteriovenous graft 12. The membrane 102 may be, for instance, a flap that allows fluid flow in one direction from the graft 12 into the vein 16. The membrane 102 may be formed from a single piece of film or may be formed from multiple segments. For example, in one embodiment, the film can include one or more slits that permit fluid flow in one direction.

The arteriovenous graft system in FIG. 5 provides various advantages. For example, in the embodiment shown in FIG. 5, only the first valve device 24 needs to be manually opened or closed.

In the embodiment shown in FIG. 5, the first valve device is represented as a balloon valve. It should be understood, however, that the first valve device may be any of the other valve devices shown and described above.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A subcutaneous arteriovenous graft system comprising:
an arteriovenous graft having an arterial end and an opposite venous end; and
at least one valve device positioned at the arterial end of the arteriovenous graft, the valve device comprising an inflatable balloon in communication with the arteriovenous graft, the valve device having a closed position when the inflatable balloon is inflated and wherein, when the valve device is in the closed position, blood flow through the arteriovenous graft is prevented in order to minimize arterial steal.

2. A system as defined in claim 1, further comprising a second valve device positioned at the venous end of the arteriovenous graft, the second valve device also comprising an inflatable balloon, wherein the first valve device and the second valve device substantially prevent blood flow through the arteriovenous graft when the respective balloons are inflated.

3. A system as defined in claim 2, wherein the inflatable ballon of the first valve device and the inflatable balloon of the second valve device have an annular shape that surrounds the arteriovenous graft.

4. A system as defined in claim 3, wherein each valve further comprises an outer collar surrounding each respective inflatable balloon.

5. A system as defined in claim 2, wherein the first valve device is capable of preventing blood flow when exposed to systolic arterial pressure in between about 170 mmHg to about 270 mmHg.

6. A system as defined in claim 2, wherein each of the valve devices further comprise an injection port in fluid communication with each of the inflatable balloons, each of the injection ports defining a diaphragm configured to receive a hypodermic needle for injecting or withdrawing fluid from each respective balloon.

7. A system as defined in claim 1, further comprising a second valve device positioned at the venous end of the arteriovenous graft, the second valve device comprising a check valve.

8. A system as defined in claim 7, wherein the check valve comprises a membrane positioned within the arteriovenous graft.

9. A system as defined in claim 8, wherein the membrane includes a slit that only allows fluid flow in one direction.

10. A system as defined in claim 8, wherein the membrane comprises a moveable flap that only allows fluid flow in one direction.

11. A system as defined in claim 7, wherein the check valve only permits fluid flow out of the arteriovenous graft through the venous end.

12. A system as defined in claim 1, further comprising an injection port in fluid communication with the inflatable balloon, the injection port defining a diaphragm configured to receive a hypodermic needle for injecting or withdrawing fluid from the balloon.

13. A system as defined in claim 12, wherein the injection port comprises a metal housing, the diaphragm being located on one surface of the housing.

14. A system as defined in claim 1, wherein the arteriovenous graft is made from a material comprising a fluoropolymer.

15. A system as defined in claim 1, wherein the valve device is positioned at a location that is less than about 20 mm from the intersection of the arteriovenous graft and an artery.

16. A system as defined in claim 1, wherein the inflatable balloon comprises a multi-layered segment located at the arterial end of the arteriovenous graft, the multi-layered segment comprising an inner layer and an outer layer, the inner layer constricting flow through the arteriovenous graft when a fluid is fed in between the inner layer and the outer layer.

17. A system as defined in claim 1, wherein the inflatable balloon is positioned in operative association with a piston, wherein, when inflated, the balloon forces the piston against the arteriovenous graft for constricting same.

18. A system as defined in claim 1, wherein the inflatable balloon is made from a material comprising silicone.

19. A system as defined in claim 1, wherein the inflatable balloon constricts the arteriovenous graft when inflated with from about 2 ccs to about 6 ccs of fluid.

20. A subcutaneous arteriovenous graft system comprising:
an arteriovenous graft having an arterial end and an opposite venous end;
a first valve device positioned at the arterial end of the arteriovenous graft, the valve device comprising an inflatable balloon, the inflatable balloon being positioned so as to prevent blood flow through the arteriovenous graft when inflated, the inflatable balloon being in communication with a first injection port, the injection port defining a diaphragm configured to receive a hypodermic needle for injecting or withdrawing fluid from the balloon, the injection port being configured to be implanted subcutaneously;

a second valve device positioned at the venous end of the arteriovenous graft, the second valve device comprising an inflatable balloon, the inflatable balloon being positioned so as to prevent blood flow through the arteriovenous graft when inflated, the inflatable balloon being in communication with a second injection port, the second injection port defining a diaphragm configured to receive a hypodermic needle for injecting or withdrawing fluid from the inflatable balloon, the second injection port also being configured to be implanted subcutaneously.

21. A system as defined in claim 20, wherein the first valve device is positioned at a location that is less than about 20 mm from the intersection of the arteriovenous graft and an artery and wherein the second valve device is positioned graft at a location that is less than about 20 mm from the intersection of the arteriovenous graft and a vein.

22. A system as defined in claim 20, wherein the inflatable balloon of the first valve device and the inflatable balloon of the second valve device have an annular shape that surrounds the arteriovenous graft, each of the inflatable balloons being surrounded by an outer collar.

23. A process for reducing arterial steal and graft thrombosis in an arteriovenous graft comprising:

providing an arteriovenous graft having been subcutaneously implanted in a patient, the arteriovenous graft including an arterial end in fluid communication with an artery and a venous end in fluid communication with a vein, the arteriovenous graft further comprising at least one valve device positioned at the arterial end of the graft;

closing the first valve device at the arterial end of the arteriovenous graft and thereby stopping blood flow through the arteriovenous graft;

injecting into the arteriovenous graft through a hypodermic needle a blood compatible fluid for flushing the arteriovenous graft and evacuating blood from the graft;

removing the hypodermic needle from the arteriovenous graft.

24. A process as defined in claim 23, wherein the arteriovenous graft further comprises a second valve device positioned at the venous end of the graft and wherein the process further comprises the step of closing the second valve device after the arteriovenous graft has been flushed with the blood compatible fluid.

25. A process as defined in claim 24, wherein the first valve device and the second valve device both include an inflatable balloon, the inflatable balloon being positioned so as to restrict blood flow through the arteriovenous graft when inflated.

26. A process as defined in claim 25, wherein the inflatable balloon of the first valve device and the inflatable balloon of the second valve device have an annular shape that surrounds the arteriovenous graft.

27. A process as defined in claim 26, wherein the first valve device and the second valve device each further comprise an outer collar surrounding each respective inflatable balloon.

28. A process as defined in claim 25, wherein the first valve device and the second valve device each further comprise an injection port in fluid communication with each respective inflatable balloon, each injection port defining a diaphragm configured to receive a hypodermic needle for injecting or withdrawing fluid from each respective balloon.

29. A process as defined in claim 24, wherein the first valve device and the second valve device each comprise a magnetically activated piston, wherein, when a magnetic field is placed in close proximity to each valve device, each respective piston is moved for opening or closing the valve device.

30. A process as defined in claim 29, wherein the first valve device and the second valve device each open or close when exposed to a changing magnetic field, each valve device further comprising a coil member configured to convert a changing magnetic field into an electric current, the coil member being in communication with a solenoid, the solenoid being configured to move each respective piston and open or close each respective valve device when an electric current is received from the respective coil member.

31. A process as defined in claim 24, wherein the first valve device is positioned so as to restrict blood flow through the arteriovenous graft at a location that is less than about 20 mm from the intersection of the arteriovenous graft and the artery and wherein the second valve device is positioned so as to restrict blood flow through the arteriovenous graft at a location that is less than about 20 mm from the intersection of the arteriovenous graft and the vein.

32. A process as defined in claim 24, wherein the first valve device and the second valve device each comprise a piston in communication with a fluid chamber, wherein, when a fluid is forced into each respective fluid chamber, each respective piston closes which in turn constricts the arteriovenous graft.

33. A process as defined in claim 24, wherein the second valve device comprises a check valve.

34. A process as defined in claim 23, wherein the blood compatible fluid comprises a saline solution.

35. A subcutaneous arteriovenous graft system comprising:

an arteriovenous graft having an arterial end and an opposite venous end;

a first valve device positioned at the arterial end of the arteriovenous graft, the first valve device including a closed position that prevents blood flow through the arteriovenous graft; and a second valve device positioned at the venous end of the arteriovenous graft, the second valve device comprising a check valve.

36. A system as defined in claim 35, wherein the first valve device comprises a fluid actuated valve or a magnetically actuated valve.

37. A system as defined in claim 35, wherein the check valve comprises a membrane located within the arteriovenous graft, the membrane only allowing fluid flow out through the venous end of the graft.

* * * * *

UNITED STATES PATENT AND TRADEMARK OFFICE
CERTIFICATE OF CORRECTION

| | | |
|---|---|---|
| PATENT NO. | : 7,025,741 B2 | Page 1 of 1 |
| APPLICATION NO. | : 10/456697 | |
| DATED | : April 11, 2006 | |
| INVENTOR(S) | : David L. Cull | |

It is certified that error appears in the above-identified patent and that said Letters Patent is hereby corrected as shown below:

Column 9, line 61 (Claim 3), "... ballon of the first valve device...," should be --... balloon of the first valve device ...--

Column 11, line 19 (Claim 21) "... graft at a location that is less than ..." should be --... at a location that is less than ...--

Signed and Sealed this

Third Day of July, 2007

JON W. DUDAS
*Director of the United States Patent and Trademark Office*